United States Patent
Inoue

[11] Patent Number: 6,099,465
[45] Date of Patent: Aug. 8, 2000

[54] ELECTROMAGNETICALLY COUPLED ELECTRONIC ENDOSCOPE SYSTEM

[75] Inventor: Kiyoshi Inoue, Omiya, Japan

[73] Assignee: Fuji Photo Optical Co., Ltd., Saitama, Japan

[21] Appl. No.: 08/975,470

[22] Filed: Nov. 21, 1997

[30] Foreign Application Priority Data

Dec. 4, 1996 [JP] Japan ................................ 8-340473

[51] Int. Cl.$^7$ ........................................................ A61B 1/05
[52] U.S. Cl. ............................ 600/134; 600/132; 348/75
[58] Field of Search ............................... 600/118, 131, 600/132, 134; 348/65, 75, 76

[56] References Cited

U.S. PATENT DOCUMENTS

| | | | |
|---|---|---|---|
| 4,384,775 | 5/1983 | Hosoda | 600/132 |
| 4,853,772 | 8/1989 | Kikuchi | 600/109 |
| 4,868,647 | 9/1989 | Uehara et al. | 600/134 |
| 5,139,021 | 8/1992 | Sekii | 600/300 |
| 5,174,293 | 12/1992 | Hagiawara | 600/425 |
| 5,434,615 | 7/1995 | Matumoto | 348/518 |
| 5,671,738 | 9/1997 | Thornberg | 600/134 |
| 5,716,323 | 2/1998 | Lee | 600/134 |
| 5,735,794 | 4/1998 | Koeda | 600/132 |
| 5,873,816 | 2/1999 | Kagawa et al. | 600/134 |

FOREIGN PATENT DOCUMENTS

| | | | |
|---|---|---|---|
| 3739445 | 7/1988 | Germany | A61B 1/06 |
| 4-146715 | 5/1992 | Japan . | |
| 4-288118 | 10/1992 | Japan . | |
| 5-176884 | 7/1993 | Japan . | |
| 5-228112 | 7/1993 | Japan . | |

*Primary Examiner*—John P. Leubecker
*Attorney, Agent, or Firm*—Snider & Associates; Ronald R. Snider

[57] ABSTRACT

An electronic endoscope system which is configured to eliminate the necessity to mount separate airtight means on a connector section between an electronic endoscope and an external unit at a stage of washing and disinfection, and maintain electrical isolation for patients' securities at the same time. The electronic endoscope system has a composition wherein an electronic endoscope which is equipped with a CCD is connected by way of a connector to a light source unit which is equipped with a light source and performs output control of at least video signals, signal transfer between the electronic endoscope and the light source unit is performed with optical elements, and electric power is supplied from the light source unit to the electronic endoscope by spatial electromagnetic means. Electric power obtained by the electromagnetic coupling means is accumulated once in a battery and the electronic endoscope is driven by the battery. In the electronic endoscope, output signals from the CCD are used as inputs for generating almost completed video signals which are to be used as monitor output video signals by a DSP.

6 Claims, 4 Drawing Sheets

ELECTROMAGNETICALLY COUPLED ELECTRONIC ENDOSCOPE SYSTEM

BACKGROUND OF THE INVENTION

This application claims the priority of Japanese Patent Application No. 8-340473 filed on Dec. 4, 1996, which is incorporated herein by reference.

1. Field of the Invention

The present invention relates to an electronic endoscope system, and more specifically contents of a connector section for electronic endoscope systems which is configured to connect an electronic endoscope as a scope to an external unit such as a light source unit and permits omitting electrical connection.

2. Description of the Prior Art

An electronic endoscope system is an instrument which leads rays from a light source unit to an electronic endoscope used as a scope, projects these rays from a tip section into a body to be observed and picks up an image of an interior of the body to be observed with a CCD (charge coupled device) or the like disposed in the tip section. In an electronic endoscope system of this kind, an electronic endoscope is connected to external units such as a light source unit and an image processor unit by way of cables and connectors, and video signals are supplied through this processor unit to a monitor.

Since a conventional electronic endoscope system, an endoscope used in the medical field in particular, requires a cleaning process at which cleaning and disinfection are carried out, a connector section which connects the electronic endoscope to the processor unit is configured so as to allow separate airtight means such as a waterproof cap to be disposed on a terminal section at the stage of washing and disinfection. However, this airtight means is relatively large and heavy, thereby posing problems that it makes inconvenient handling of the electronic endoscope and that it makes a cleaning work tedious.

An optical connector section which connects the electronic endoscope to the light source unit, in contrast, has no exposed terminal for electrical connection and, when a waterproof structure is adopted for the connector section, it can be washed and disinfected without attaching such special airtight means as that described above. Accordingly, the washing and disinfection works are facilitated if the electronic endoscope system and the external unit can be connected in a manner similar to the optical connector section described above.

Further, it is required for the electronic endoscope system to adopt isolation means which electrically separates internal circuits in an electronic endoscope and so on to assure patients' securities, and it is desired to dispose this isolation means so as to be highly efficient.

Furthermore, since electronic endoscopes of various types are adopted in accordance with locations and purposes of application, it is conventionally general to manufacture light source units and processor units for electronic endoscopes of each type. Accordingly, an external unit such as a light source unit which is connectable and usable commonly to and with endoscopes of different types, if available, makes it possible to obtain an electronic endoscope having a high utility value.

BRIEF SUMMARY OF THE INVENTION

The present invention has been achieved in view of the problems described above and has an object to provide an electromagnetically coupled electronic endoscope system which eliminates the necessity to dispose separate airtight means on a connector section between an electronic endoscope and an external unit at a stage of a cleaning work, permits establishing electrical isolation for assuring patients' securities at the same time, and is connectable and usable commonly to and with electronic endoscopes of different types.

For accomplishing the object described above, the electronic endoscope system according to the present invention is characterized in that it comprises an electronic endoscope configured as a scope equipped with an image pickup device, an external unit to which the electronic endoscope is connected by way of a connector, and electromagnetic coupling means (a spatial transformer) which is disposed at a location of the connector and supplies electric power from the external unit to the electronic endoscope in an electrically isolated condition.

Another electronic endoscope system according to the present invention is characterized in that it comprises an electronic endoscope configured as a scope equipped with an image pickup device, an external unit which is connected to the electronic endoscope by way of a connector, equipped with a light source and controls at least video signal outputs, optical interface means which performs signal transfer between the external unit and the electronic endoscope with optical elements, and electromagnetic coupling means which is disposed at a location of the connector and supplies electric power from the external unit to the electronic endoscope in an electrically isolated condition.

In the electronic endoscope system which has the configuration described above, control signals related to image pickup operations and video signals are transferred through optical interface means which is composed by combining light emitting elements and light receiving elements, and the electric power is supplied to the electronic endoscope through the spatial electromagnetic coupling means which requires no connecting terminal. Accordingly, the electronic endoscope system makes it possible to carry out washing and disinfection without disposing a separate waterproof cap or the similar member over a connector section between the electronic endoscope and the external unit, and obtain an electrically isolated condition for assuring patients' securities.

When almost all signal processor circuits for generating monitor output video signals are disposed on a side of the electronic endoscope in this case, processings which are peculiar to individual endoscopes having different characteristics of objective optical systems and CCDs thereof, can be completed in the electronic endoscope, whereby it is sufficient for the external unit to output rays and perform simple control operations. Accordingly, the electronic endoscope system is connectable and usable commonly to and with electronic endoscopes of different types.

The electronic endoscope according to the present invention can be equipped with a battery which is charged with the electric power supplied from the electromagnetic coupling means and drive the electronic endoscopes with this battery.

Further, the electronic endoscope system according to the present invention makes it possible to dispose a connector section of a light guide for leading rays from the light source, an optical connector section for video signals for the optical interface means and an optical connector for control signals collectively in a single connector section.

DETAILED DESCRIPTION OF THE PREFERRED EMBODIMENTS

Figure 1:
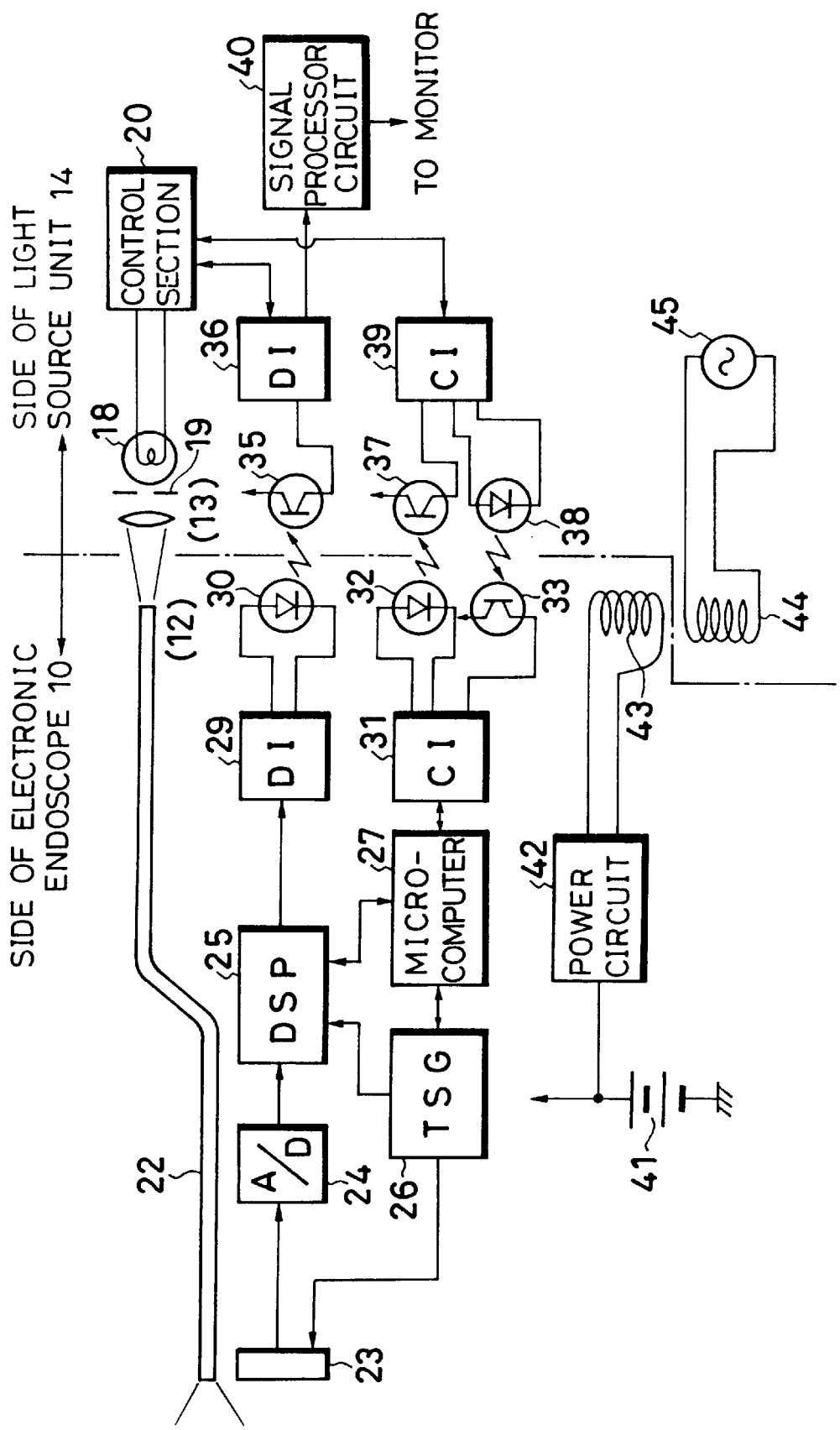
FIG. 1 is a block diagram illustrating a circuit configuration in an embodiment of the electronic endoscope system according to the present invention.
Figure 2:
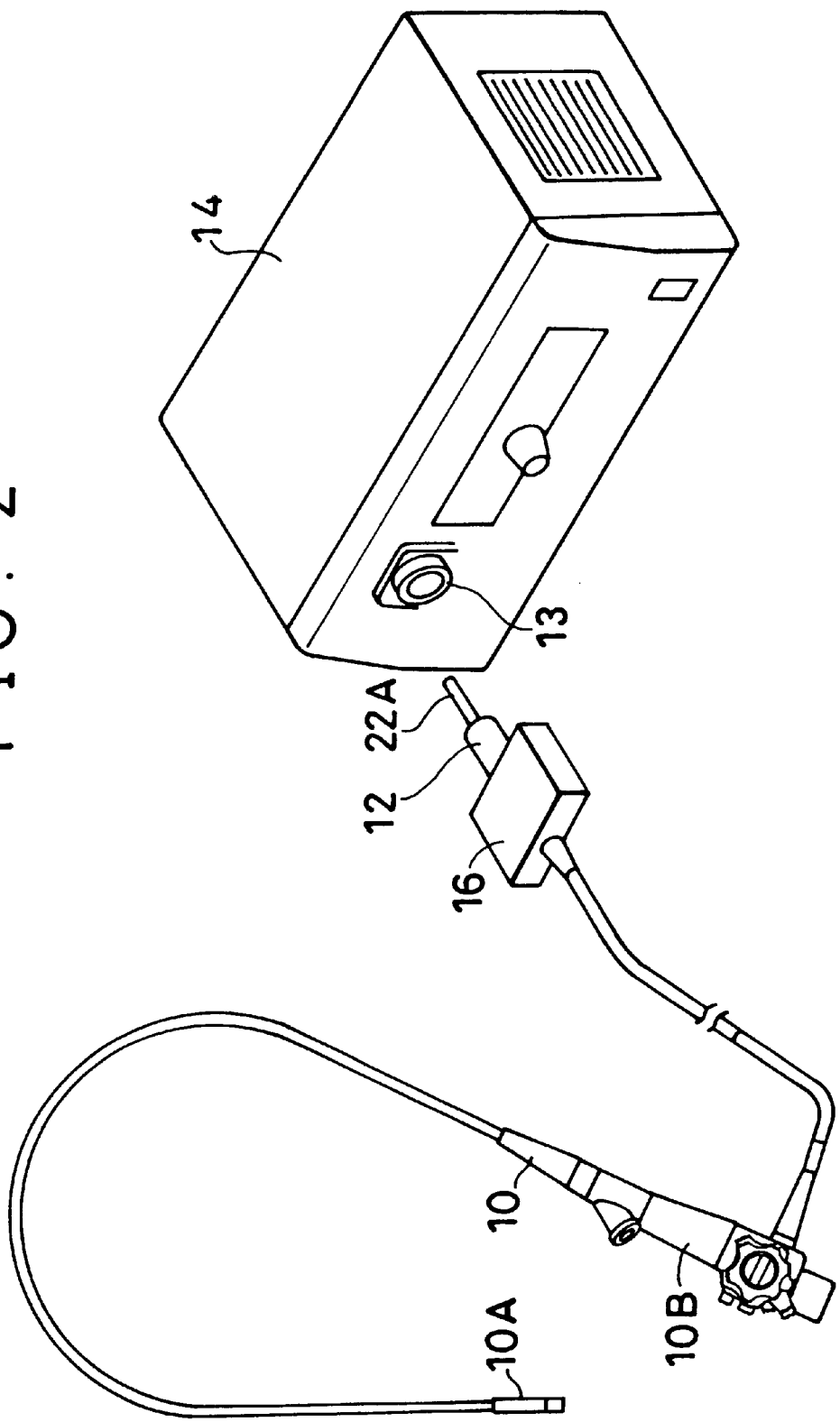
FIG. 2 is an external appearance illustrating an overall configuration of the embodiment of the electronic endoscope system according to the present invention.

A configuration of an embodiment of the electronic endoscope system according to the present invention is illustrated in FIGS. 1 through 4: FIG. 1 being a block diagram illustrating a circuit configuration, FIG. 2 being a perspective view illustrating an overall appearance of the electronic endoscope system, FIG. 3 being a perspective view illustrating an external appearance of a connector section and FIG. 4 being a sectional view of the connector section. In FIG. 2 first, an electronic endoscope 10 which is equipped with a tip section 10A in which an image pickup device is disposed and a manipulating section 10B is connected to a light source unit 14 adopted as an external unit by way of a connector 12 and a receptacle 13. The light source unit 14 is composed of a conventional light source unit which is incorporated with a processor unit and a circuit section 16 is integrated with the connector 12 on the side of the electronic endoscope 10.

In FIG. 1, a light source 18 such as a xenon lamp, a movable iris stop member 19 and a control circuit 20 are disposed in the light source unit 14, and the control circuit 20 performs an output control of rays from the light source (an iris control) as well as other various kinds of controls. Rays emitted from the light source 18 are led to the tip section from the connector 12 by way of a light guide 22 disposed in the electronic endoscope 10. In the electronic endoscope 10, a CCD 23 which is an image pickup device is disposed in the tip section (10A), and an A/D converter 24, a DSP (digital signal processor) 25, a timing signal generator circuit (TSG) 26, etc. are arranged for extracting video signals from the CCD 23 and performing image processings. The DSP 25 is capable of generating almost completed monitor output video signals which can be output to a monitor after the signals are subjected to required processings such as amplification, gamma correction and white balance processing as well as conversion into analog signals with a signal processor circuit (40) which is described later.

Further, there is arranged a microcomputer 27 which executes, for example, a freeze (still image) operation and outputs signals for the iris control from luminance signals of the video signals. In addition, there are disposed a memory for temporarily storing the video signals and other members which are not shown.

Optical interface means is disposed as signal transfer means between the electronic endoscope 10 and the light source unit 14. Speaking more concretely, disposed on the side of the electronic endoscope 10 are a digital interface (DI) 29 and light emitting element 30 such as a light emitting diode which are connected to the DSP 25 as well as a communication interface (CI) 31, a light emitting element 32 and a light,receiving element 33 such as a phototransistor which are connected to the microcomputer 27: these optical elements 30, 32 and 33 being arranged in the connector 12. Though the circuit elements other than the optical elements described above are disposed in the circuit section 16 in this embodiment, these elements may be disposed in the manipulating section 10B without using the circuit section 16.

On the other hand, arranged on the side of the light source unit 14 are a light receiving element 35 such as a phototransistor which receives rays output from the light emitting element 30, a digital interface (DI) 36, a light receiving element 37 which receives rays output from the light emitting element 32, a light emitting element 38 which transmits optical signals to the light receiving element 33 and a communication interface (CI) 39: these optical elements 35, 37 and 38 being disposed in the receptacle 13. Digital video signals which are output from the digital interface 36 are converted into analog signals by a signal processor circuit 40 and then output to a monitor or the similar unit.

Further, the electronic endoscope 10 is configured to be driven with a battery, a secondary battery 41 of several to ten-odd volts is adopted for driving the electronic endoscope and a power circuit (charging circuit) 42 is connected to the secondary battery 41.

Electromagnetic coupling means (a spatial transformer) is disposed for supplying electric power to this power circuit 42 in a condition where it is free from a direct electrical connection. This electromagnetic coupling means is composed of a secondary winding 43 which is disposed on the side of the electronic endoscope 10, and a primary winding 44 which is disposed on the side of the light source unit 14 and kept in a condition electrically isolated from the secondary winding 43.

An AC power source 45 is connected to the primary winding 44.

Figure 3:
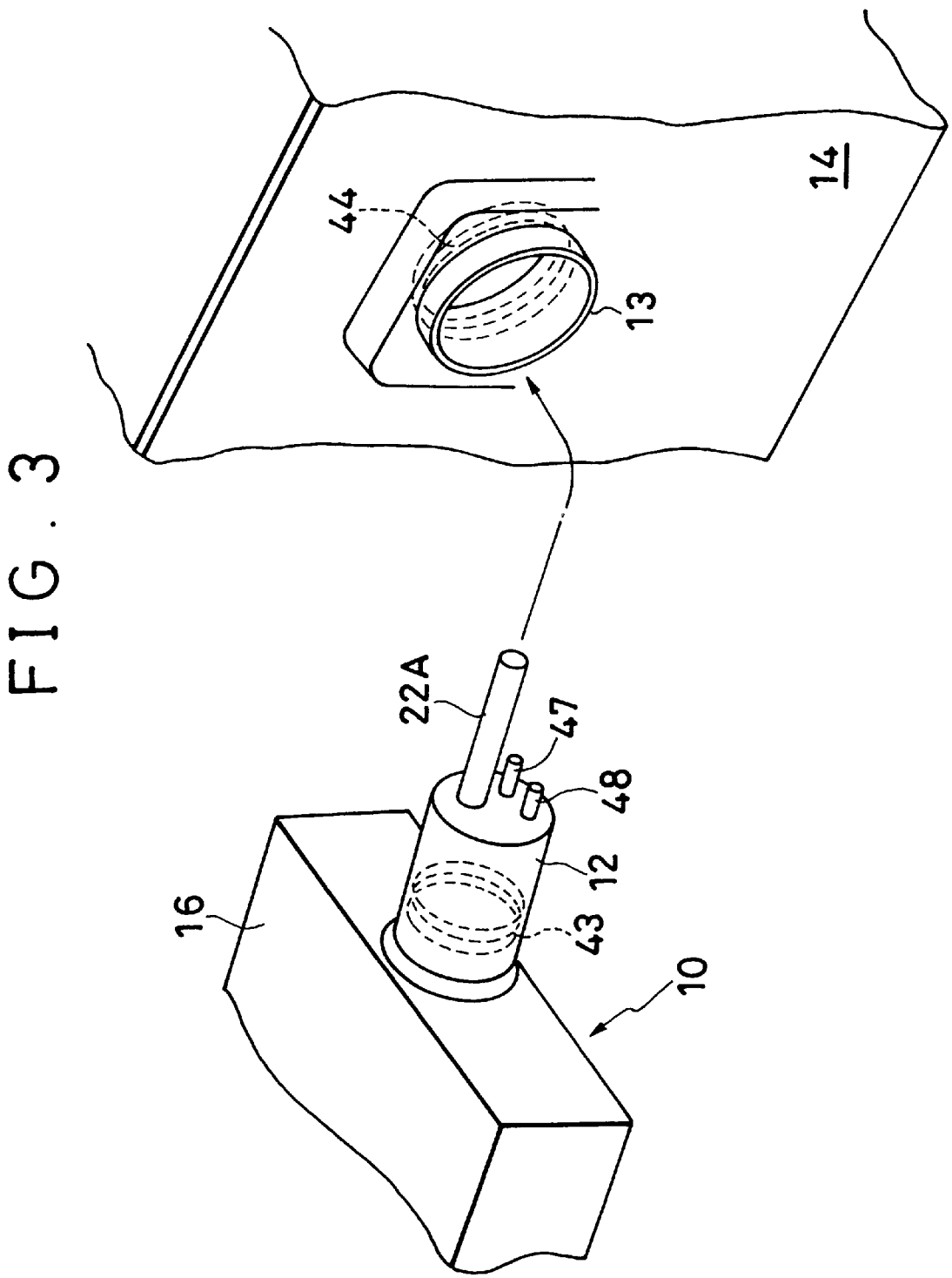
FIG. 3 is an external appearance illustrating structures of portions of the connector section shown in FIG. 2.

A configuration of the connector section is shown in FIG. 3. On the connector 12 which is disposed on the side of the electronic endoscope 10, an input end (connector portion) 22A of the light guide 22 is formed so as to protrude therefrom, and an optical connector section 47 for the video signals and an optical connector section 48 for the control signals are disposed under the input end. These optical connector sections 47 and 48 are attached to the connector 12 with water proof structures which are not shown but similar to a waterproof structure adopted for attaching the input end 22A. The light emitting element 30 described above is attached to the optical connector section 47 for the video signals, and the light emitting element 32 and the light receiving element 33 described above are attached to the other optical connector section 48 for the control signals.

Figure 4:
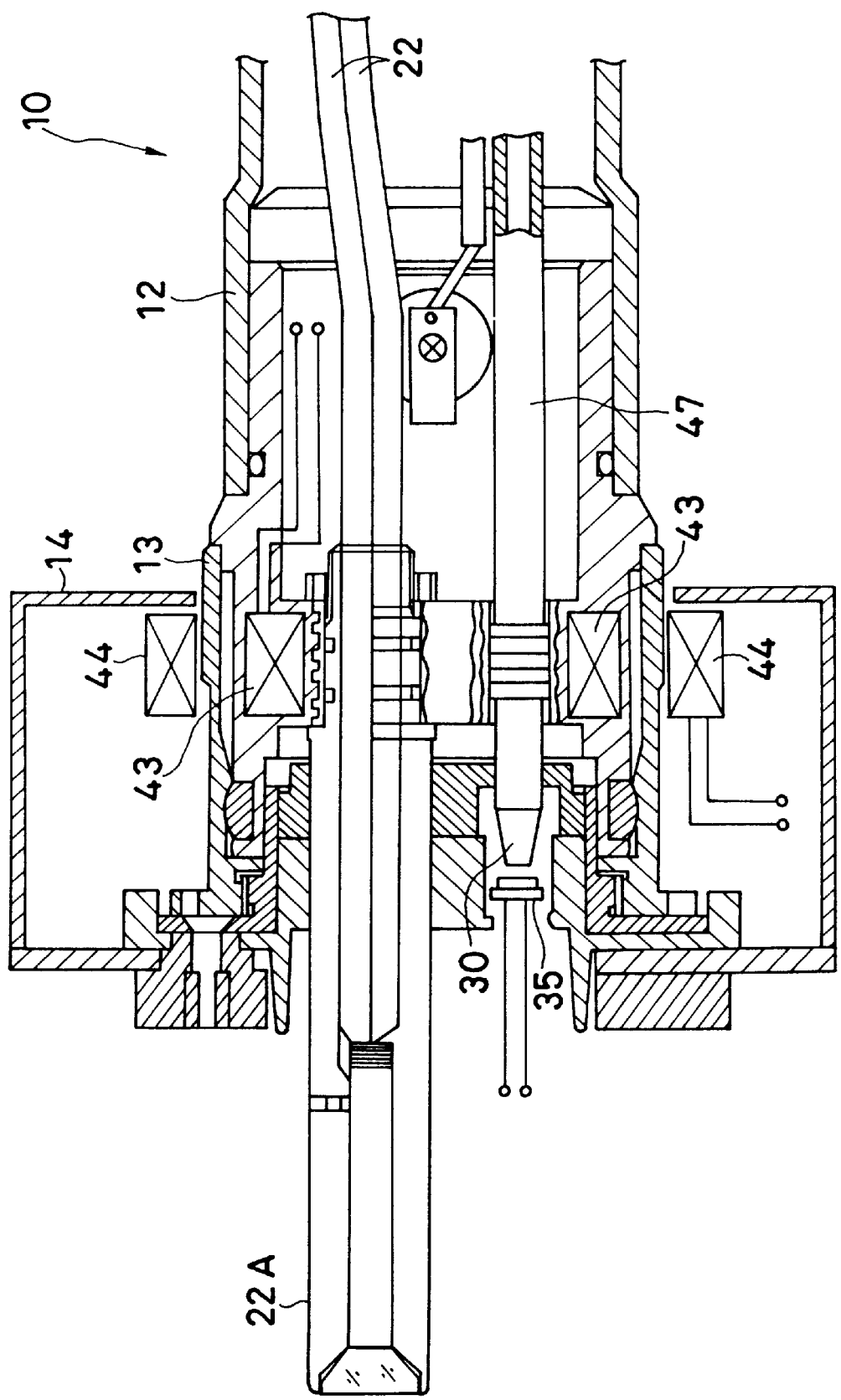
FIG. 4 is a sectional view illustrating the connector portions shown in FIG. 3 in a condition where they are coupled.

FIG. 4 shows a structure of the connector section in a condition where the connector and the receptacle are connected to each other. When the connector 12 is connected to the receptacle 13, the input end 22A of the light guide 22 described above is inserted to the light source unit (18) in the light source unit and the optical connector section 47 for the video signals which has the light emitting element 30 attached to a tip thereof is disposed so as to oppose to the light receiving element 35. Further, the secondary winding 43 on the side of the electronic endoscope 10 is disposed so as to be embedded inside an outer cylinder of the connector 12, whereby the winding 43 is set in an airtight condition from a view point of waterproofness and the primary winding 44 on the side of the light source unit 14 is also disposed inside a connecting tube of the receptacle 13. When the connector is attached to the receptacle, the secondary winding 43 is disposed inside the primary winding 44 in the receptacle 13, whereby the windings are electromagnetically coupled with each other by way of a space, thereby forming the spatial transformer.

The embodiment has the configuration described above or illustrated in FIG. 1, wherein electric power from the AC power source 45 on the side of the light source unit 14 is supplied to the side of the electronic endoscope 10 through the electromagnetic coupling formed by way of the space between the primary winding 44 and the secondary winding 43, thereby charging the secondary battery 41 for a time which is controlled by the power circuit 42 and while the endoscope is used. All the circuits disposed in the electronic endoscope 10 are driven by electric power of the secondary battery 41.

On the other hand, the control signals from the control section 20 on the side of the light source unit 14 are supplied to the microcomputer 27 in the electronic endoscope 10 by way of the communication interface 39, the light emitting element 38 and the light receiving element 33 which are used as optical communication means, and the communication interface 31. The control signals from the microcomputer 27 are transferred to the side of the light source unit 14 also by way of the communication interfaces 31 and 39, the light emitting element 32 and the light receiving element 37. For example, control signals associated with a start and a termination of acquisition of the video signals from the CCD 23 as well as control signals for controlling an amount of rays are transferred.

Speaking concretely, the DSP 25 described above generates color difference signals and luminance signals as video signals on the basis of output signals from the CCD 23, and the microcomputer 27 described above outputs iris control signals corresponding to the luminance signals from the DSP 25 to the side of the light source unit 14. Then, the iris stop 19 is driven by the control section 20 for adjusting an amount of rays output from the light source on the side of the light source unit, thereby controlling brightness on a screen at a constant level.

The DSP 25 described above generates almost completed video signals, which are transmitted by way of the digital interface 29, the light emitting element 30, the light receiving element 35 and the digital interface 36, processed into analog signals by the signal processor circuit 40 and output to the monitor.

As understood from the foregoing description, the embodiment allows all the signal transfer lines to be connected through the optical elements and permits connecting power lines by way of the spatial transformer between the electronic endoscope 10 and the light source unit 14 which is equipped with the video signal output function and other control functions, thereby making it possible to completely eliminate parts which are electrically connected directly. When the waterproof structures described above are adopted for the connector 12, it is therefore possible to protect the internal electric members from washing water and the like, thereby eliminating the necessity to attach a separate waterproof cap or the similar means at a stage of washing and disinfection.

Further, the embodiment allows electrical isolation to be established between the electronic endoscope 10 and the light source unit 14, thereby making it possible to assure electrical security for patients at the same time.

Furthermore, the DSP 25 described above is configured to generate the almost completed monitor output video signals, thereby making it possible to connect and use electronic endoscopes of different types which use objective optical systems and CCDs having different characteristics commonly to and with the same light source unit 14.

Though a pair of the light emitting element 30 and the light receiving element 35 are disposed on the optical connector portion 47 for the video signals, and the two pairs of the light emitting elements 32, 38 and the light receiving elements 33, 37 are disposed on the optical connector portion 48 for the control signals in the embodiment described above, it is possible, by transferring the control signals during a blanking period of the video signals, to dispose a pair of light emitting element and a light receiving element on the optical connector portion 48 for the control signals, or transfer all the signals using only a pair of a light emitting element and a light receiving element.

Though the embodiment described above is configured to drive the electronic endoscope 10 with the secondary battery 41, it is possible, on the premise that the spatial transformer (43, 44) is used, to drive the electronic endoscope 10 with a power source having the conventional configuration wherein the secondary battery 41 is not used.

As understood from the foregoing description, the electronic endoscope system according to the present invention which is configured to transfer signals between the electronic endoscope and the external unit through the optical interface means and supply electric power through the spatial electromagnetic coupling means provides a merit to eliminates the necessity to mount a waterproof cap on a connector section between an electronic endoscope and an external unit at a stage of washing and disinfection, and another merit to permit establishing electrical isolation for assuring electrical securities for patients at the same time.

Furthermore, owing to the fact that a signal processor circuit for generating the almost completed video signals which are to be used as the monitor output video signals is disposed in the electronic endoscope described above, the electronic endoscope system according to the present invention is connectable and usable commonly to and with electronic endoscopes of different types.

What is claimed is:

1. An electromagnetically coupled electronic endoscope system comprising:
   an electronic endoscope which is configured as a scope equipped with an image pickup device;
   an external unit which is connected to said electronic endoscope by way of a connector;
   electromagnetic coupling means which is disposed at a location of a connector and supplies electric power from said external unit to a side of said electronic endoscope in an electrically isolated condition; and
   said electromagnetic coupling means having a primary winding which is disposed in a connector receptacle on the side of the external unit and a secondary winding which is embedded inside an outer cylinder of the connector on the side of the electronic endoscope wherein when said external unit is connected to said endoscope, said windings are electromagnetically coupled to each other.

2. An electromagnetically coupled electronic endoscope system comprising:
   an electronic endoscope which is configured as a scope equipped with an image pickup device;
   an external unit which is connected to said electronic endoscope by way of a connector, equipped with a light source and performs output control of at least video signals;
   optical interface means which performs signal transfer between said external unit and said electronic endoscope with optical elements;
   electromagnetic coupling means which is disposed at a location of said connector and supplies electric power from said external unit to said electronic endoscope in an electronically isolated condition; and said electromagnetic coupling means having a primary winding which is disposed in a connector receptacle on the side of the external unit and a secondary winding which is embedded inside an outer cylinder of the connector on the side of the electronic endoscope wherein when said external unit is connected to said endoscope, said windings are electromagnetically coupled to each other.

3. An electronic endoscope system according to claim 2, wherein a signal processor circuit for generating almost completed video signals as monitor output video signals from output signals of said image pickup device is disposed in the electronic endoscope.

4. An electronic endoscope system according to claim 2, wherein said electronic endoscope system comprises a battery which is charged with electric power supplied from said electromagnetic coupling means, and wherein said electronic endoscope is driven by said battery.

5. An electronic endoscope system according to claim 2, further comprising:

control signals for the optical interface means;

a connector section for a light guide;

an optical connector for video signals;

an optical connector section for the control signals; and wherein the connector section of a light guide for leading rays from said light source, the optical connector section for video signals and the optical connector section for the control signals for said optical interface means are disposed collectively in a same connector.

6. An electronic endoscope system according to claim 5, wherein said connector section of the light guide, said optical connector section for video signals and the control signals are disposed collectively in the same water proof connector.

* * * * *